US009983287B2

United States Patent
Djeridane et al.

(10) Patent No.: US 9,983,287 B2
(45) Date of Patent: May 29, 2018

(54) SYSTEM AND METHOD FOR ESTIMATING A QUANTITY OF INTEREST OF A DYNAMIC ARTERY/TISSUE/VEIN SYSTEM

(71) Applicant: OLEA MEDICAL, La Ciotat (FR)

(72) Inventors: Fayçal Djeridane, Marseilles (FR); Timothé Boutelier, La Ciotat (FR)

(73) Assignee: OLEA MEDICAL, La Ciotat (FR)

( * ) Notice: Subject to any disclaimer, the term of this patent is extended or adjusted under 35 U.S.C. 154(b) by 0 days. days.

(21) Appl. No.: 15/146,073

(22) Filed: May 4, 2016

(65) Prior Publication Data

US 2016/0245889 A1 Aug. 25, 2016

Related U.S. Application Data

(63) Continuation of application No. PCT/FR2015/052728, filed on Oct. 9, 2015.

(30) Foreign Application Priority Data

Oct. 13, 2014 (FR) ...................... 14 59822

(51) Int. Cl.
*G06K 9/00* (2006.01)
*G01R 33/563* (2006.01)
(Continued)

(52) U.S. Cl.
CPC ...... *G01R 33/56366* (2013.01); *A61B 5/0263* (2013.01); *A61B 5/0275* (2013.01);
(Continued)

(58) Field of Classification Search
CPC ......... A61B 6/507; A61B 6/481; A61B 5/742; G06T 2207/30104; G06T 7/0012; G06T 2207/30101
See application file for complete search history.

(56) References Cited

U.S. PATENT DOCUMENTS 6,628,743 B1   9/2003  Drummond et al.
8,837,800 B1 *  9/2014  Bammer ................ G06T 7/003
                                        382/130
(Continued)

FOREIGN PATENT DOCUMENTS

FR   2 979 453 A1   3/2013

OTHER PUBLICATIONS

Nordli et al.,Voxel-specific brain arterial input functions from dynamic susceptibility contrast MRI and blind deconvolution in a group of healthy males, Mar. 2010, ISSN: 0284-1851 (Print) 1600-0455 (Online) Journal homepage: http://www.tandfonline.com/loi/iard20,Acta Radiologica, 51:3, pp. 334-343.*

(Continued)

*Primary Examiner* — Vu Le
*Assistant Examiner* — Guillermo Rivera-Martinez
(74) *Attorney, Agent, or Firm* — Buchanan Ingersoll & Rooney PC

(57) ABSTRACT

The invention relates to a system and method for estimating a quantity of interest from perfusion data resulting from the acquisition of a plurality of a patient volumes or stations. Such a method may include a step for triggering the output of said quantity of interest in the form of a consolidated map by means of an adapted man-machine interface.

12 Claims, 5 Drawing Sheets

(51) Int. Cl.
- A61B 6/00 (2006.01)
- A61B 5/026 (2006.01)
- A61B 5/0275 (2006.01)
- A61B 5/055 (2006.01)
- G01R 33/56 (2006.01)
- A61B 6/03 (2006.01)
- G06T 7/62 (2017.01)
- A61B 6/04 (2006.01)

(52) U.S. Cl.
CPC .............. *A61B 5/055* (2013.01); *A61B 6/032* (2013.01); *A61B 6/481* (2013.01); *A61B 6/486* (2013.01); *A61B 6/507* (2013.01); *A61B 6/5217* (2013.01); *G01R 33/5601* (2013.01); *G01R 33/56383* (2013.01); *G06T 7/62* (2017.01); *A61B 6/0457* (2013.01); *G06T 2207/30024* (2013.01); *G06T 2207/30104* (2013.01)

(56) References Cited

U.S. PATENT DOCUMENTS

| | | | | |
|---|---|---|---|---|
| 2002/0111550 | A1* | 8/2002 | Schwamm | A61B 5/0263 600/419 |
| 2008/0114234 | A1* | 5/2008 | Gering | G01R 33/546 600/411 |
| 2011/0035198 | A1* | 2/2011 | McGrath | A61B 5/055 703/2 |
| 2011/0110488 | A1* | 5/2011 | Lardo | A61B 6/032 378/12 |
| 2011/0150309 | A1* | 6/2011 | Barfett | G06T 7/11 382/131 |
| 2013/0123611 | A1* | 5/2013 | Riederer | G01R 33/4818 600/419 |
| 2013/0329973 | A1* | 12/2013 | Cao | A61B 5/0033 382/128 |
| 2014/0266195 | A1* | 9/2014 | Levin | G01R 33/56509 324/309 |
| 2015/0051476 | A1* | 2/2015 | Fenchel | A61B 5/0035 600/411 |
| 2015/0208930 | A1* | 7/2015 | Gall | A61B 5/0263 600/420 |

OTHER PUBLICATIONS

Wang et al., Correction of Arterial Input Function in Dynamic Contrast-Enhanced MRI of the Liver, Aug. 2012, J Magn Reson Imaging; 36(2): 411-421.*

International Search Report (PCT/ISA/210) dated Jan. 21, 2016, by the European Patent Office as the International Searching Authority for International Application No. PCT/FR2015/052728.

Written Opinion (PCT/ISA/237) dated Jan. 21, 2016, by the European Patent Office as the International Searching Authority for International Application No. PCT/FR2015/052728.

Justin D. Anderson et al., "1042 Multi-Modality Magnetic Resonance Demonstrates Factors Critical to Functional Capacity in Peripheral Arterial Disease", Journal of Cardiovascular Magnetic Resonance, vol. 10, No. Suppl 1, Oct. 22, 2008, pp. 1-3, XP021400149.

* cited by examiner

SYSTEM AND METHOD FOR ESTIMATING A QUANTITY OF INTEREST OF A DYNAMIC ARTERY/TISSUE/VEIN SYSTEM

The invention relates to a system and method for estimating a quantity of interest from perfusion data resulting from the acquisition of a plurality of a patient's volumes or stations. The invention is notably different from known methods by its accuracy and by highly consistent estimated parameters linked to a plurality of stations, particularly to study organs.

The invention is based, in particular, on Perfusion Weighted Magnetic Resonance Imaging (PW-MRI) or Computed Tomography (CT) imaging techniques. These techniques can quickly obtain valuable information on the hemodynamics of organs found in humans or animals. This information is particularly crucial for a practitioner seeking to establish a diagnosis and to make therapeutic decisions in the treatment of pathologies.

To perform such techniques, a Nuclear Magnetic Resonance or Computed Tomography imaging device 1, such as that shown by way of the non-limiting example in FIGS. 1 and 2, is generally used. It can provide a plurality of sequences of digital images 12 of one or more parts of the body such as, by way of non-limiting examples, the brain, the heart, the lungs, etc. Said device applies to that a high-frequency electromagnetic waves combination on the body part under consideration and measures the signal retransmitted by some atoms, such as, by way of a non-limiting example, hydrogen for Nuclear Magnetic Resonance Imaging. Consequently, the device allows determining the chemical composition and thus the nature of biological tissues in each elementary volume, such as a voxel, of the imaged volume. The Nuclear Magnetic Resonance or Computed Tomography imaging device 1 is operated using a console 2. A user can select parameters 11 to control the device 1. A plurality of sequences of digital images 12 of a part of a body of a human or animal is obtained from information 10 generated by device 1. The Nuclear Magnetic Resonance Imaging device 1 may be optionally included in an imaging analysis system.

Alternatively, the device 1 can be dissociated from the analysis system. According to this alternative, the image sequences 12 may optionally be stored in a server 3 and constitute a medical record 13 of a patient. Such a record 13 may include images of different types, such as images of perfusion or diffusion. Image sequences 12 are analyzed using a dedicated processing unit 4. Said processing unit comprises means to communicate with the outside world to collect images. Said means to communicate further allow the processing unit 4 to deliver ultimately, through output means 5 offering a graphic rendering, audible or other, to a practitioner 6 or a researcher, an estimate of one or more quantities of interest, optionally formatted in the form of a content, such as hemodynamic parameters 14, from the digital images 12, preferably images of perfusion, by means of an adapted man-machine interface. User 6, preferably a practitioner, of the analytical system can thus prove or disprove a diagnosis, decide on a therapeutic action he deems appropriate, conduct further research, etc. Optionally, the user 6 can set the operation of the processing unit 4 or the output means 5 by parameters 16. For example, he can set display thresholds or choose the estimated parameters he wishes to view. There is a variant, described in connection with FIG. 2, wherein an imaging system, as described above, further comprises a preprocessing unit 7 for analyzing image sequences, to derive experimental signals 15 (perfusion or permeability) and outputting them to the processing unit 4 which is thus relieved of this task. Furthermore, to achieve an estimate of hemodynamic parameters or, more generally, a quantity of interest, the processing unit 4 typically includes processing means, such as a calculator, to perform an estimating method in the form of a computer program preloaded in storage means which cooperate with said processing means.

Perfusion images by Nuclear Magnetic Resonance or Computed Tomography are obtained by intravenously injecting a contrast agent, such as gadolinium salt for Magnetic Resonance Imaging, and recording its bowl over time at each voxel of the image, through acquisitions at regular intervals. Such images allow characterizing, in particular, blood flow in the tissue of a given organ, by following the evolution of the concentration of the contrast agent in each voxel of the volume acquired over time. According to the invention and throughout this document, the term "voxel" (contraction of "volumetric pixel"), means an elementary volume for measuring the definition of a matrix digital image in three dimensions. Such a voxel can also be considered as a pixel in three dimensions. In all cases, such a voxel is a rectangular parallelepiped whose closed surface consists of its six faces.

For brevity, we will leave out the indices x,y,z to identify voxels. For example, instead of designating the signal for a voxel with coordinates x,y,z on the basis of time as $S_{x,y,z}(t)$, we will simply designate it as $S(t)$. It is understood that the operations and calculations described below are generally carried out for each voxel of interest, so as to finally obtain images or maps representative of a quantity of interest, particularly hemodynamic parameters, which we seek to estimate.

A standard model allows linking the signal intensity $S(t)$ measured over time t to the concentration $C(t)$ of said contrast agent.

By way of non-limiting example, in Perfusion Computed Tomography, the signal for each voxel is directly proportional to the concentration: $S(t)=k \cdot C(t)+S_0$. In Perfusion Imaging by Nuclear Magnetic Resonance, there is an exponential relationship $S(t)=S_0 \cdot e^{-k \cdot TE \cdot C(t)}$. In both cases, $S_0$ represents the average intensity of the signal before the arrival of the contrast agent. Regarding imaging by Nuclear Magnetic Resonance, k is a constant depending on the relationship between the paramagnetic susceptibility and the concentration of the contrast agent in the tissue and TE is the echo time. The value of constant k for each voxel being unknown, the latter is set at an arbitrary value for all voxels of interest. This results in relative, not absolute, estimates. However, this information remains relevant since we are mainly interested by the relative variation of these values in space, in particular between healthy tissue and diseased tissues.

The conservation of the mass of the contrast agent in the tissue volume contained in each voxel at each instant is written as $$\frac{dC(t)}{dt} = BF \cdot [C_a(t) - C_v(t)].$$

$C_a(t)$ is the concentration of the contrast agent in the artery supplying the tissue volume (Arterial Input Function or AIF). BF (Blood Flow) is the blood flow in the tissue volume and $C_v(t)$ is the concentration of the contrast agent in the vein draining the tissue volume (Venous Output Function or VOF).

Assuming that the artery/tissue/vein dynamic system is linear and invariant over time, we can write $C_v(t)=C_a(t) \otimes h(t)$ where h(t) is the impulse response of the system and $\otimes$ designates the convolution product. A formal solution of the previous differential equation with C(t=0)=0 initial condition thus becomes $C(t)=BF \cdot C_a(t) \otimes R(t)$ where R(t) is the Residue Function defined by $$R(t) = H(t) - \int_0^t h(\tau) d\tau$$

where H is the Heaviside unit step generalized function.

The hemodynamic parameters such as BF, MTT or BV as well as the residue function R(t) are currently estimated as follows, in the case of perfusion imaging by Nuclear Magnetic Resonance.

For each voxel, the experimental perfusion signal $S_{exp}(t)$, sampled at the times of measurement $t_i$, i=1,N, is converted to a concentration curve C(t). From the concentration curve C(t), and assuming that the associated theoretical arterial input function $C_a(t)$ is known, the product $BF \cdot R(t)$ is estimated by numerical deconvolution.

Various approaches have been considered to obtain the theoretical arterial input functions $C_a(t)$ in order to subsequently deconvolve the concentration curves C(t).

In a first approach, an experimental global arterial input function is manually selected by the practitioner. It can be measured, for example, at an artery near the organ to be studied.

According to another approach, local arterial input functions are automatically obtained from perfusion images using signal processing techniques and selection criteria. For example, the "best" function is sought in the immediate vicinity of the current tissue voxel where we wish to estimate the hemodynamic parameters or additional distribution functions. The purpose of this approach is to ultimately get estimates that are less biased and more accurate by overcoming, at least in part, delay and dispersion problems.

Once the arterial input functions $C_a(t)$ are obtained, it is necessary to deconvolve the concentration curves to estimate the function of residues R(t) and to derive hemodynamic parameters, such as blood flow BF, mean transit time MTT or blood volume BV.

To perform the deconvolution operation of the experimental concentration curve C(t) by the theoretical arterial input function $C_a(t)$ obtained by the methods described above, two approaches are generally used.

One approach is a parametric deconvolution.

We seek to model the voxel by several separate compartments mutually exchanging the contrast agent. In this way, parametric models $R(t, \Theta_R)$ for residues functions are introduced, $\Theta_R$ being the vector of said models parameters, said models being dependent on the hemodynamic parameters of the voxel. These models are fitted to experimental signals, for example by the Bayes method.

Several known parametric models are then used to describe the concentration curves of the contrast agent in each voxel. By way of non-limiting example, the simplest model is the Kety model, which uses the following premise: each voxel is separated into two compartments, the intravascular space and the extravascular space, said compartments each occupying respectively a fraction of voxel $v_a$ and $v_e$, equally and respectively characterized by a contrast agent concentration $C_a(t)$ and $C_e(t)$. Thus, the Kety model is usually written in the integral form: $C(t)=K_{trans}C_a(t) \otimes e^{-k_{ep}t}$ where $K_{trans}$ is the blood flow, $k_{ep}$ is the time constant characterizing the transfer between the two compartments, $\otimes$ designates the convolution product and $C_a(t)$ is the arterial input function.

The set of hemodynamic parameters of such a model is $\theta_{hem}=\{K_{trans}, k_{ep}\}$. Furthermore, the blood volume $v_e$, other hemodynamic parameter, is defined by the central volume theorem as follows:

$$v_e = \frac{K_{trans}}{k_{ep}}.$$

Other models can account more accurately for the physiological processes occurring in the voxel, by introducing more complex functions of residues, as well as additional hemodynamic parameters, such as the Kety-Tofts or extended Tofts-Kermode model, the St. Lawrence and Lee model, etc.

Once the model is selected and, consequently, the type of residue function is fixed, the arterial input function must also be chosen. Choosing said function has proven decisive for estimating hemodynamic parameters: generally, the practitioner or the imaging system selects the concentration curve of the contrast agent of a voxel located at an artery as a function arterial input of all voxels of the volume studied. Subsequently, the convolution product between the arterial input function and the residue function is calculated numerically by discretizing it on the temporal acquisition grid of the perfusion data. The theoretical concentration of the contrast agent C(t) at every moment of the acquisition $t_i$ is written based on the hemodynamic parameters $\theta_{hem}$: $C(t_i)=f(t_i, \theta_{hem})$. Different methods are applicable to estimate the hemodynamic parameters $\theta_{hem}$ from the contrast agent concentration curves within each voxel. A method of estimating such a parameter performed by a processing unit of a system, such as that described in connection with FIG. 1 or 2, comprises a step for minimizing the sum of square errors between the model and the experimental measurements using the following formula: $\hat{\theta}_{hem}=\arg\min \Sigma[C^{exp}(t_i)-f(t_i, \theta_{hem})]^2$. The minimization is performed numerically, preferably by executing a non-linear optimization algorithm.

After estimating hemodynamic parameters for each voxel of interest, results may be presented in the form of parameters maps, thus highlighting different tissue types, namely healthy or pathological, based on the values of said parameters.

A second approach is a broader approach based on non-parametric deconvolution: no model assumption is made for the residue function.

The standard convolution model $C(t)=BF \cdot C_a(t) \otimes R(t)$ is first temporally discretized in the following format: c=BFAr where,
 c is the vector containing the concentration of contrast agent at the acquisition times,
 BF is the blood flow
 r is the function vector of the discretized residues,
 A is the convolution matrix dependent on the arterial input function.

As explained above in the case of the first approach described, the arterial input function must be selected correctly in relation to the voxels studied, so as to allow the construction of the convolution matrix A.

Such discretization can be done, for example, using the approximation of the rectangular rule:

$$\forall\, i = 1, N,$$
$$C(t_i) = BF \cdot \int_0^{t_i} C_a(\tau) \cdot R(t-\tau)\, d\tau \approx BF \cdot \Delta t \cdot \sum_{k=0}^{i} C_a(t_i) \cdot R(t_i - t_k)$$

where $\Delta t$ is the sampling period. We are thereby reduced to a linear system $Ad=C$ by setting $$A = \Delta t \cdot \begin{pmatrix} C_a(t_1) & 0 & \cdots & 0 \\ C_a(t_2) & C_a(t_1) & \ddots & \vdots \\ \vdots & \vdots & \ddots & 0 \\ C_a(t_N) & C_a(t_{N-1}) & \cdots & C_a(t_1) \end{pmatrix}$$

$$b = \begin{vmatrix} R(t_1) \\ R(t_2) \\ \cdots \\ R(t_N) \end{vmatrix}$$

$$c = \begin{vmatrix} C(t_1) \\ C(t_2) \\ \cdots \\ C(t_N) \end{vmatrix}$$

$$d = BF \cdot b$$

In practice, the matrix A is poorly conditioned and almost singular, so we cannot reverse this linear system digitally without risking to obtain meaningless solutions and outlier estimates. We must therefore resort to various methods to obtain, for example, a pseudo-inverse $\tilde{A}^{-1}$ of the matrix A and thereafter an estimate $\hat{d}$ of d by $\hat{d} = \tilde{A}^{-1} \cdot c$. Among these methods for obtaining a pseudo-inverse performed by the processing unit of an imaging system such as that described in connection with FIG. 1 or 2, we can cite the Truncated Singular Value Decomposition ((T)SVD) or the Simple Singular Value Decomposition (sSVD) and the Hunt deconvolution in the frequency domain. The document should not be limited solely to the mentioned techniques.

More generally, such a method to estimate a quantity of interest is to minimize a criterion of the type $\|Ad-c\|^2 + \|\Gamma d\|^2$ where $\|\Gamma d\|^2$ is a regularization term emphasing certain solutions and to obtain an estimate of d by $$\hat{d} = \underset{d}{\mathrm{argmin}}(\|Ad - c\|^2 + \|\Gamma d\|^2).$$

Among these methods, we can mention Tikhonov regularization, the use of the wavelet transform, etc.

Once $\hat{d}$ is obtained, the processing unit can perform a method for estimating $\hat{BF}$ of BF by $\hat{BF} = \hat{d}(t_1) = \hat{d}(0)$ since, by definition, $R(0)=1$. There are many variants of such methods based on arterial input function(s): for example, experimental arterial input functions can be previously adjusted to a parametric or semi-parametric theoretical model $C_a(t, \Theta_a)$ where $\Theta_a$ is a vector of parameters, in order to artificially increase the signal-to-noise ratio.

Other hemodynamic parameters can be estimated once the Residue function R(t) itself, such as the Mean Transit Time (MTT) through the voxel, that can be expressed using the following formula: $MTT = \int R(t)dt \approx \Delta t \Sigma r_i$. The blood volume (BV) in the voxel can also be calculated using the theorem of the central volume: $BV = BF \cdot MTT$ Nowadays, the technical constraints of imaging devices by Nuclear Magnetic Resonance or Computed Tomography, as illustrated by way of example in FIGS. 1 and 2, only provide and/or acquire images with acquisition fields limited to a few square centimeters. The volume delivered by the various acquisitions and analysis of image sequences is thus restricted and known techniques of perfusion imaging analysis, in particular Nuclear Magnetic Resonance or Computed Tomography, are suitable for the study of "small" organs such as, by way of non-limiting examples, the brain or the heart, or the study of a limited portion of the body. On the other hand, such techniques become inadequate or ineffective for the study of larger sized organs that cannot be covered by the fields of acquisition of an imaging device, such as, by way of non-limiting examples, the spinal cord, or the study of the entire body, especially, as a non-limiting example, to track the onset and/or development of metastases which may be located throughout the body.

A "naive" way to solve this problem would be to perform as many perfusion examinations, in particular acquisitions, as necessary to fully cover the volume one wishes to analyze. In this case, the total acquisition time, particularly the one spent by the patient in imaging devices, would be multiplied by the number of sub-volumes required to analyze the whole volume of interest, thus greatly increasing the total duration of examinations: such examinations would become very burdensome and more difficult to bear by the patient. In principle, analysis by Computed Tomography may consist in measuring the X-ray absorption by the tissues of the various voxels. By applying the protocol described above, the radiation dose received by a patient during the implementation of such a protocol would be greatly increased, making the examination very dangerous for said patient as a result of overexposure to said radiation.

In addition, for each acquisition of sub-volume, an injection of contrast agent would be necessary. Although such a contrast agent would allow improving the quality of diagnostics by medical Magnetic Resonance Imaging, toxicity at high concentrations of such contrast agent could be problematic for a patient. The amount of contrast agent that a patient can tolerate being limited, such an approach is inappropriate, or even potentially dangerous.

Other experimental protocols, such as, by way of non-limiting example, the experimental acquisition protocol of Professors Rahmouni and Luciani, were implemented to allow the study of perfusion imaging of the whole body, especially by Magnetic Resonance Imaging. Such protocols were developed especially for the study of myeloma, a form of cancer affecting the cells of the spinal cord. The size of the spinal column, and consequently of the spinal cord, being well beyond the field of vision and/or acquisition of imaging devices by Magnetic Resonance, conventional methods used in principle for perfusion imaging of this organ are not adapted.

To obtain a dynamic tracking of the contrast agent in the entire spine after a single injection of said agent, the acquisition can take place, for example, according to the following protocol: a patient is typically lying on a movable table, generally motorized, moving in the field of vision of the Magnetic Resonance Imaging device. After a first volume, also known as "station", corresponding to a field of acquisition of the imaging device, has been scanned by the Magnetic Resonance Imaging device, the patient is moved within said imaging device by means of said movable table, so that a second station or volume contained in the acquisition field, optionally adjacent to the first volume or station previously analyzed, is the subject of an acquisition. By way of non-limiting example, such a protocol is illustrated in connection with FIG. 3. In this example, five successive stations I to V, three sagittal stations I, II, IV and two coronal stations III, V are subject of acquisitions, said stations being numbered in the order of acquisitions: a sixty-second period is necessary to sample the five volumes and return to the first volume. Such a period is divided into an image acquisition sub-period of about thirty-nine seconds and a sub-period of about twenty-one seconds of movement of the movable table. Each voxel of interest in the overall volume is sampled every sixty seconds. The resulting concentration curves thus have a temporal resolution of sixty seconds.

According to such a protocol, the perfusion data acquired and associated with each volume or station are subsequently processed to estimate the quantity of interest, such as, by way of non-limiting examples, hemodynamic parameters. A "natural" approach is to consider each station independently of each other, by applying conventional methods as described above, i.e. parametric or nonparametric approaches. For the parametric approach for example, a model, such as the Ketty model, as a non-limiting example, and an arterial input function can be selected for each station. The hemodynamic parameters, such as, for example, the parameters $K_{trans}$, $k_{ep}$ and $v_e$ are therefore estimated and the associated data maps can also be produced.

However, this "natural" method gives rise to little or no comparable results from one station to another. For example, the average value of $K_{trans}$ measured in the lumbar vertebrae L1 may vary from simple to double depending on the station from which the acquisition is made. This variability can also be observed for the other parameters $k_{ep}$ and $v_e$. The results thus obtained by using such a protocol, applying known estimation methods, are therefore not reproducible, making the data obtained by said acquisition protocol of little use, or even totally unusable. Indeed, by applying an independent analysis for each station, it hides the fact that the voxels of each volume were acquired sequentially at different times. For example, for the protocol described above, the station IV is acquired fifteen seconds after the station III. The arterial input function specific to each station is thus not sampled at the same times, and each station appears to have a different arterial input function. Consequently, the arterial input function of each station is modelled according to a different model, valid only in the acquisition instants of the station to which it is attached, as described in connection with FIG. 4. FIG. 4 illustrates examples of arterial input functions produced and/or selected for each station I to IV, said functions being represented as a concentration curve of a contrast agent as a function of time at a selected artery. For each station I to IV, an independent arterial input function is determined automatically and/or manually. Indeed, the concentration curve of an arterial input function is characterized by a rapid rise followed by an equally rapid decrease, with a characteristic time of only a few tens of seconds. Next, a slower decrease phase is observed with a longer characteristic time. The temporal resolution of the concentration curves being of the order of one minute, it is not possible to accurately sample the rapid variations. The different arterial input functions determined in each station do not therefore reproduce all of the dynamic actually present and the last stations acquired are more affected by this effect than the first ones. Thus, the non-simultaneity of acquisitions between each station and the low temporal resolution are all reasons leading to hemodynamic parameter estimates non-reproducible from one station to another, making the analysis of large organs, such as the spinal cord, by known perfusion imaging techniques, inadequate and ineffective.

The invention allows meeting all or part of the drawbacks posed by known solutions.

Among the many benefits of the invention, we can mention that allows:
- overcoming the temporal sampling of the arterial input function, by selecting a joint arterial input function for all stations analyzed;
- preserving the health of a patient by injecting a single dose of contrast agent which allows the analysis of large organs present on a plurality of stations or the whole body;
- performing analyses by perfusion imaging, of large organs, such as, by way of a non-limiting example, the spinal cord, the size of said organs being greater than the standard acquisition field of imaging analysis devices by Magnetic Resonance;
- the opportunity to check built arterial input functions;
- proposing a solution independent of all hemodynamic parameters estimation techniques;
- enabling the display and a global vision of organ maps present on several stations;
- giving reproducible results, comparable from one station to another.

To this end, a method is especially provided for producing an estimate of a quantity of interest of an artery/tissue/vein dynamic system of an organ elementary volume—called a voxel. Such a method is intended to be performed by processing means of a processing unit of a perfusion imaging analysis system, and comprises a step for estimating said quantity of interest from perfusion data related to a plurality of stations. According to the invention, such a method comprises a step for building a joint arterial input function from perfusion data related to at least one station among said plurality of stations, each station being a volume corresponding to an acquisition field defined by a medical imaging device. Furthermore, said step for estimating the quantity of interest uses said built joint arterial input function.

According to a preferred embodiment, the invention provides that the step for building a joint arterial input function can include a step for determining an arterial input function specific to each station among said at least one station, the joint arterial input function being built from said specific arterial input function.

Advantageously, when the perfusion imaging analysis system comprises output means for a user of said system, said output means cooperating with the processing unit, said method may comprise a subsequent step for causing an output of the joint arterial input function by said output means.

To improve the quality of perfusion data, the invention provides that the method may include a preliminary step for preprocessing the perfusion data, said step being designed to correct said perfusion data.

According to a second subject-matter, the invention relates to a method for producing an estimate of a quantity of interest of an artery/tissue/vein dynamic system of a region of interest, said region comprising at least one voxel. According to the invention, said quantity of interest is estimated by voxel by means of a method according to the first subject-matter of the invention.

To analyze an organ whose size or configuration exceeds the acquisition field of the perfusion imaging analysis device, said region of interest may extend over several stations among said plurality of stations.

Advantageously, when the perfusion imaging analysis system comprises output means for a user of said system, said output means cooperating with the processing unit, said method may comprise a subsequent step for causing an output of said quantity of interest estimated for the voxels of the region of interest by said output means.

According to a third subject-matter, the invention relates to a processing unit comprising means to communicate with the outside world and processing means cooperating with storage means. The means to communicate are able to receive from the outside world perfusion data linked to a plurality of stations, each station being a volume corresponding to an acquisition field defined by a medical imaging device, and the storage means comprise instructions executable or interpretable by the processing means, the interpretation or the execution of said instructions by said processing means causes the implementation of a process according to the invention.

To allow a practitioner to make a diagnosis and make a quick decision, the communication means of the processing unit of the invention can deliver an estimated quantity of interest in a suitable format to output means able to output to a user.

According to a fourth subject-matter, the invention relates to a perfusion imaging analysis system having a processing unit according to the invention and output means adapted to output to a user an estimated quantity of interest according to a method of the invention and performed by said processing unit.

According to a fifth subject-matter, the invention relates to a computer program product comprising one or more interpretable or executable instructions by the processing means of a processing unit according to the invention. Said processing unit further includes storage means or cooperates with such storage means, said program being loadable into said storage means. The interpretation or the execution of said instructions by said processing means causes the implementation of a method for estimating a quantity of interest according to the invention.

Other features and advantages will become clearer after reading the following description and examining the accompanying figures in which:

FIGS. 1 and 2, previously described, show two alternative embodiments of a medical imaging analysis system;

FIG. 3, previously described, shows images of perfusion, obtained by an imaging device by Nuclear Magnetic Resonance in connection with several imaged stations of a human being after injection of a contrast agent;

FIG. 4, previously described, shows examples of arterial input functions determined for four stations, in the form of concentration curves C(t) of a contrast agent flowing within a voxel of an artery as a function of time;

Figures 5A, 5B:
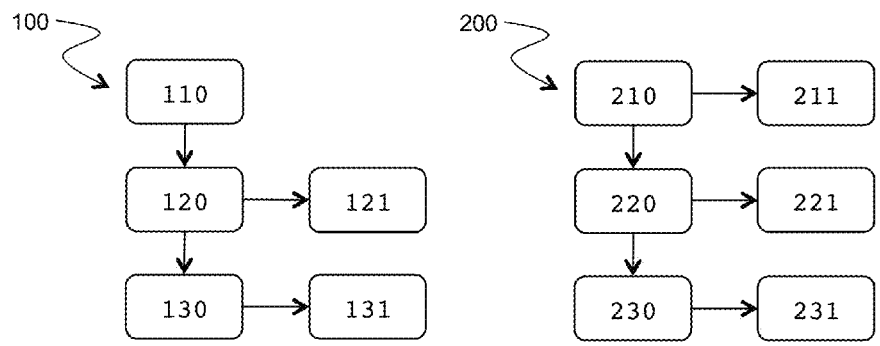
FIGS. 5a and 5b show simplified flow diagrams of methods in accordance with the invention.

FIG. 5a shows an example of a simplified algorithm of method 100—according to the invention—for producing an estimate of a quantity of interest of an artery/tissue/vein dynamic system of an organ elementary volume—called a voxel. Such a method 100 may be performed by a processing unit of a perfusion imaging analysis system, such as the system described in connection with FIG. 1 or 2 and adapted accordingly.

The method 100 according to the invention mainly comprises a step 130 for estimating a quantity of interest, by way of non-limiting examples, a hemodynamic parameter or the residue function, from perfusion data linked to a plurality of stations. Within the meaning of the invention, the term "station" designates a volume corresponding to the acquisition field of a medical imaging device, such as the device 1 of the perfusion imaging analysis system described in connection with FIG. 1 or 2. Thus, each station is linked to or associated with a volume corresponding to an acquisition field defined by a medical imaging device. Said acquisition field may or not be, depending on the variants, associated with a particular position of the movable table of the medical imaging device on which the patient is generally lying. Within the meaning of the invention, the term "perfusion data" designates all the images or signals acquired at several times by a medical imaging device in order to study the evolution of a previously injected contrast agent in the body of a patient. Such data may advantageously consist of image sequences, such as the image sequences 12 described in connection with FIG. 1 or 2. As mentioned above in connection with FIGS. 1 and 2, the perfusion data may advantageously be stored in a server at the time of their acquisition so that they can be processed later by a user of an imaging analysis system, preferably a practitioner. Perfusion data are advantageously linked to or associated with a particular station.

According to the invention, prior to the estimation of hemodynamic parameters 130, in order to overcome the temporal sampling of the arterial input function, such a method 100 comprises a step 120 for building a joint arterial input function from perfusion data linked to at least one station among said plurality of stations. However, building such arterial input function in accordance with step 120 may not be limited to the perfusion data in connection with a single station: in fact, in order, for example, for fitting a model function of arterial input closer to reality and refine the construction of said joint arterial input function, perfusion data can be linked or associated with two or more stations, namely as much as stations available. By way of non-limiting example, as described in connection with FIG. 3, the perfusion data can come from the five stations I to V to construct a joint arterial input function.

Figure 3:
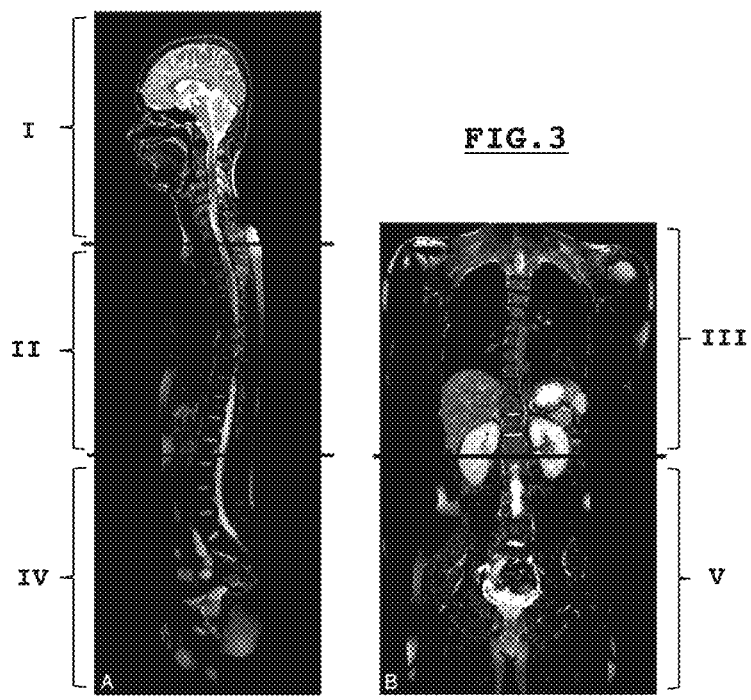
Figure 4:
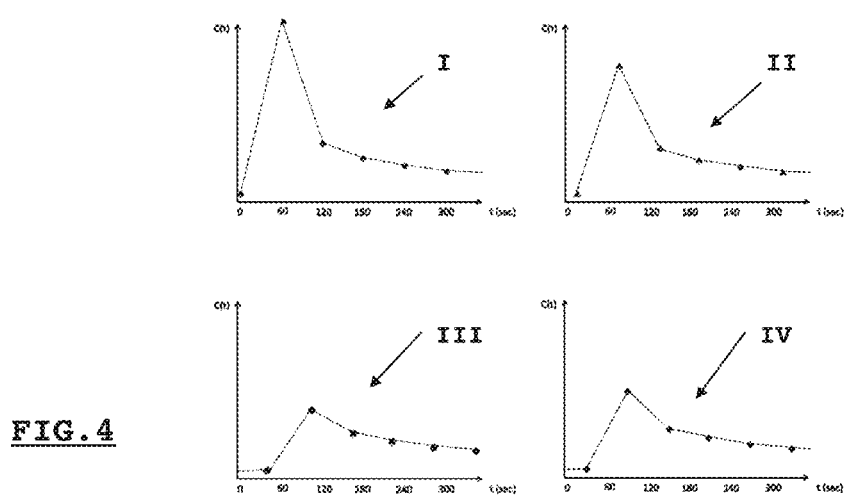
Figure 6:
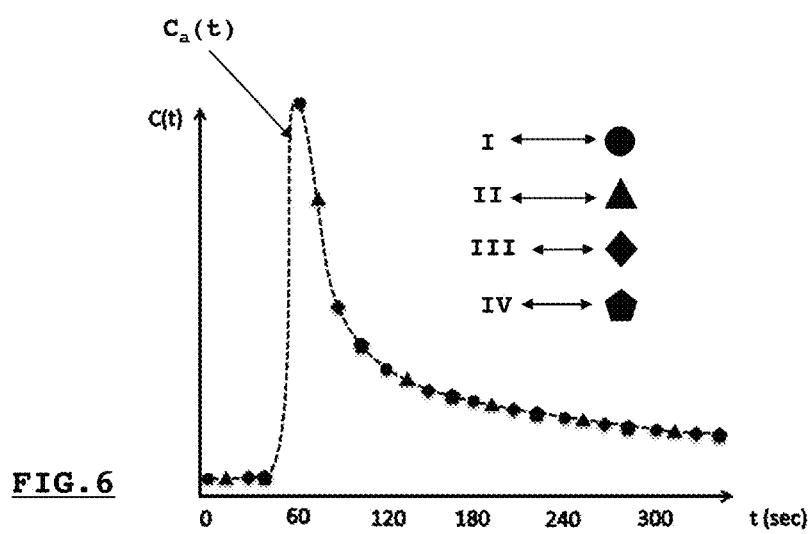
FIG. 6 shows an example of an arterial input function built from the perfusion data of four stations, in accordance with the invention.

FIG. 6 shows an example of an arterial input function built from four stations I to IV of the five acquired, said stations being defined by FIG. 3 and acquired according to the experimental protocol of acquisition of Prof. Rahmouni and Luciani.

Generally, the built joint arterial input function is advantageously unique for all stations: such arterial input function can be described by an analytic function given as $C_a(t,\theta_a)$ where $\theta_a$ is the set of the parameters of the arterial input function. Such parameters $\theta_a$ are estimated in 120 from the perfusion data of different stations and are the same for all voxels of all stations. Such an estimate of parameters $\theta_a$ can be achieved, by way of non-limiting example, by adjusting the model defined $C_a(t,\theta_a)$ on concentration curves of the contrast agent from arteries selected from all stations. Said arteries can be selected manually or automatically according to the chosen protocol. Alternatively or additionally, parameters $\theta_a$ may also be adjusted in conjunction with hemodynamic parameters $\theta_{hem}$ of the voxels. According to a preferred embodiment, the invention provides that step 120 for building a joint arterial input function can include a step for determining, manually or automatically, an arterial input function, specific or dedicated to a station among said at least one station, the joint arterial input function being built from said specific arterial input function. As stated previously, in order to adjust a model of arterial input function closest to reality and refine the building of said function by estimating the parameters $\theta_a$, perfusion data may be linked to or associated with two or more stations, i.e. up to as many stations as available.

A preferred such embodiment is described in connection with FIG. 6. In this example, step 120 for building a joint arterial input function $C_a(t)$ consists in adjusting said function to the measured values of contrast agent concentrations at sampling times within each station, among the stations I to IV. As specified above, said joint arterial input function can be described by an analytic function given as $C_a(t,\theta_a)$ where $\theta_a$ is the set of parameters of the arterial input function. By way of non-limiting but preferred example, such an analytical function may correspond to a bi-exponential function such as:

$$C_a(t, \Theta_a) \begin{cases} 0 & \text{if } t < \tau \\ A_1 e^{-k_1(t-\tau)} + A_2 e^{-k_2(t-\tau)} & \text{if } t > \tau \end{cases}$$

where $\theta_a = \{A_1, A_2, k_1, k_2, \tau\}$. Such a model is particularly suitable for the implementation of a method according to the invention, since it correctly reproduces the temporal characteristics of the arterial input function curve $C_a(t)$, that is to say, a sudden spike followed by a rapid decrease and finally a slower decrease.

Alternatively or additionally, the invention also provides that step 120, for building a joint arterial input function, consists in selecting, in a database of existing arterial input functions, said functions being previously measured with a sufficient temporal resolution in a population of control patients, a joint arterial input function. The choice of such oversampled arterial input function may be carried out using the perfusion data of each station.

Figure 1:
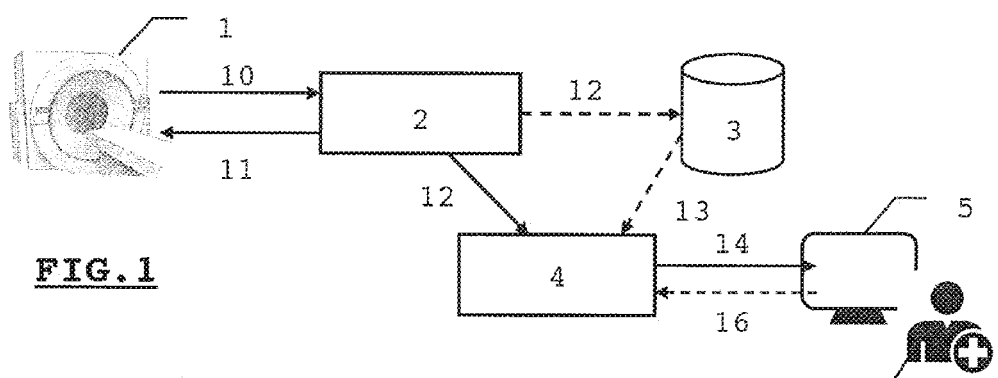
Figure 2:
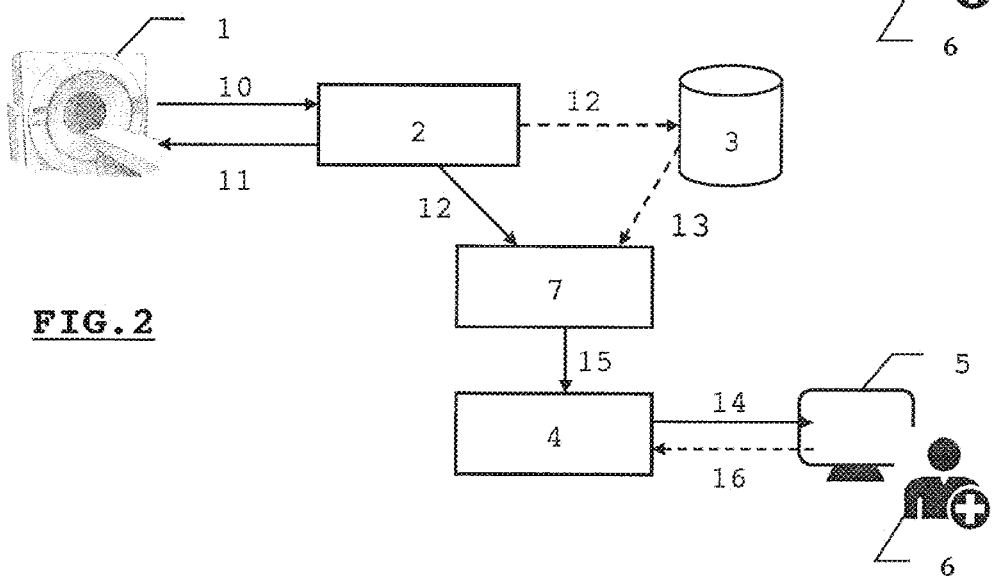

Advantageously, when the perfusion imaging analysis system described in connection with FIGS. 1 and 2, includes output means 5, such as, by way of a non-limiting example, a human-machine interface, such as a screen or other equivalent means, to a user 6 of said system, said output means 5 cooperating with the processing unit 4, said method may comprise a subsequent step 121 to cause an output of the joint arterial input function thus built by said output means. Alternatively or additionally, such a step 121 may also cause an output of the perfusion data voxels used to build the joint arterial input function. Such a step 121 allows, in particular when the voxels have been automatically selected to build the joint arterial input function, to validate the relevance of said selected voxels, that is, that the selected voxels actually correspond to voxels of interest in the arteries.

In addition, step 130 for estimating the quantity of interest, uses the built joint arterial input function: such arterial input function is valid for all stations at all times. Step 130 for estimating the quantity of interest may consist of the implementation, by the processing unit, of all known estimation techniques of hemodynamic parameters, advantageously parametric or non-parametric methods, as described above.

According to the parametric approach, for a given microcirculation model, the function of residues may be described by an analytic function given as $R(t,\theta_{hem})$ where $\theta_{hem}$ is the set of hemodynamic parameters. By way of non-limiting examples, a method for optimizing the parameters of the function, such that the least squares minimization, with or without constraint, or even a Bayesian estimation method, may advantageously be performed.

Alternatively or additionally, according to the non-parametric approach, a convolution matrix may be built from the built joint arterial input function using a finer temporal grid than that of the acquisition protocol, so as to properly sample the different time scales present in said arterial input function. By way of non-limiting examples, the SVD (Singular Value Decomposition) method may be performed. However, the Bayesian deconvolution method is preferred in view of the particularly proven accuracy of the estimates produced.

In addition, when the perfusion imaging analysis system described in connection with FIGS. 1 and 2 includes output means 5, such as, by way of a non-limiting example, a human-machine interface or any other equivalent means, for a user 6 of said system, said output means cooperating with the processing unit 4, said method may comprise a subsequent step 131 to cause an output of the estimated quantity of interest, such as, for example, hemodynamics parameters 14, in an appropriate format. By way of non-limiting examples, such a format may be a value, a color within a specific palette to express the intensity of said estimated quantity of interest, or any other equivalent means.

To increase the relevance of perfusion data, the invention provides that the method may include a preliminary step 110 for pretreatment of perfusion data, said step consisting in particular in correcting artifacts or applying any other corrective filter.

Computed Tomography imaging and, especially, Magnetic Resonance Imaging, like all other medical imaging techniques, is no exception to producing false images: artifacts. Artifacts are observable images that do not actually represent any anatomical reality. Quite often, it is necessary to attempt to avoid or minimize them by modifying certain acquisition or reconstruction parameters. Such artifacts may be of different kinds. In principle, by way of non-limiting examples, three corrections are generally applied to improve the quality of the perfusion data: a correction of patient movements or movements due to breathing, heartbeat and blood flow, a correction of the field of vision of the perfusion imaging device and/or an image denoising.

FIG. 5b shows an example of a simplified algorithm of method 200—according to the invention—to produce an estimate of a quantity of interest of an artery/tissue/vein dynamic system of a region of interest.

A method 200 is arranged to produce an estimate of a quantity of interest, by way of non-limiting examples, a hemodynamic parameter or the residue function, of an artery/tissue/vein dynamic system of a region of interest. A "region of interest" means any region with at least one voxel. Nevertheless, a region of interest should not be restricted to a single voxel, but may include a plurality of voxels, selected manually or automatically. According to the invention, said quantity of interest may be estimated for each voxel by means of a method 100 according to the invention, as described previously, performed iteratively for each voxel by the processing means of the processing unit 4. It is thus possible, according to step 210, to estimate a quantity of interest on a plurality of voxels defining a region of interest, which may optionally extend over several stations among a plurality of stations, in order to, for example, perform the analysis of organs that are larger than the acquisition field of the perfusion imaging analysis device.

Figure 7:
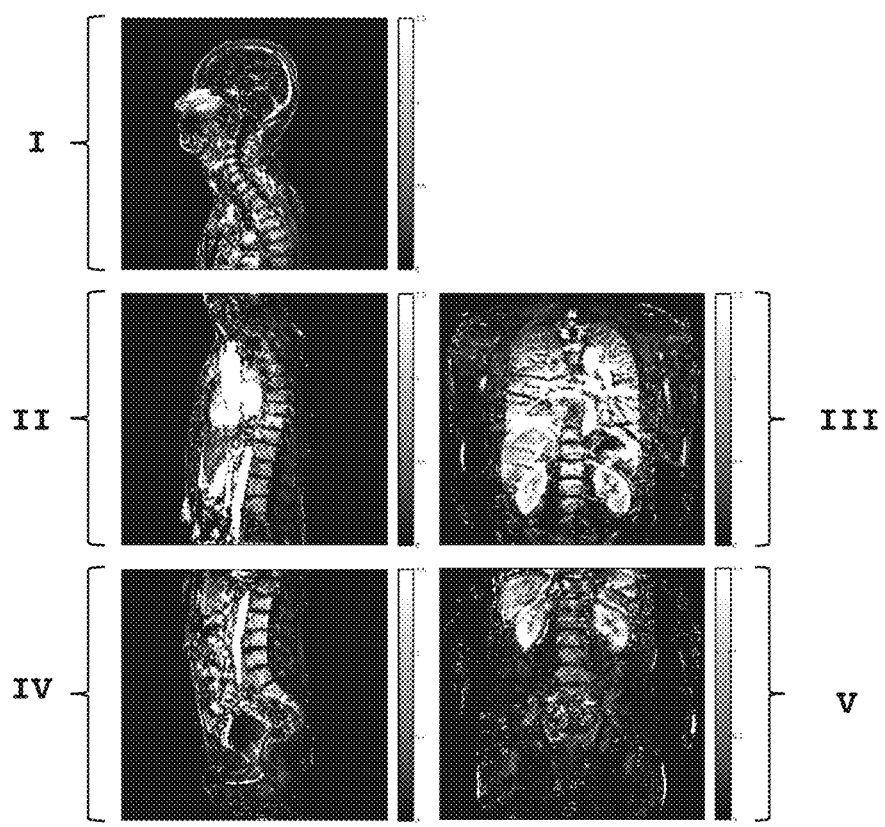
FIG. 7 shows five maps relative to the estimated blood flow from a plurality of stations according to the invention.

In addition, said method may comprise a subsequent step 211 for causing an output of said quantity of interest, namely a hemodynamic parameter 14, estimated for the voxels of the region of interest by said output means according to an appropriate format. The output may advantageously be related to a parameter map where each voxel corresponds to a degree of intensity in relation to the estimated quantity of interest. Such step may include a substep for displaying a parameter map for each station. Such an embodiment is described in connection with FIG. 7. FIG. 7 shows five maps relating to blood flow, also known as $K_{trans}$, estimated from a plurality of stations, preferably five, in accordance with the invention, the five maps corresponding to stations I to V. Such maps for the stations I to V may be advantageously used in the context of the study of myeloma, cancer affecting the cells of the spinal cord. Each station thus comprises a representation independent from one another.

Alternatively or additionally, the method 200 may include a step 220 for generating a global volume from a plurality of stations. It may also include a step for causing the output, for example in the form of a consolidated map integrating or merging the maps produced for said plurality of stations. Such a step 220 may thus comprise a sub-step for joining different station maps included in the plurality of stations. Such an embodiment is described in connection with FIG. 8.

Figure 8:
FIG. 8 shows a consolidated map relating to said estimated blood flow.

FIG. 8 shows a consolidated map of a plurality of stations from parameter maps relating to estimated blood flow, said maps shown by way of non-limiting examples in connection with FIG. 7. Two adjacent maps among the different stations I to V, generally comprise an overlap region, said overlap region preferably having corresponding peripheral voxels, corresponding in pairs and forming pairs of corresponding voxels. The quantity of interest in connection with such pairs of voxels may be estimated by the processing unit 4 as the result of a linear combination between the estimates of said quantity of interest of the corresponding voxels within the two adjacent stations. Thus, any discontinuity in the consolidated map, resulting from a fusion of parameter maps specific to each station, among the stations I to V, is prevented or attenuated: observation of the presence of such discontinuity may be verified through the output means 5 of a medical imaging device, such as that described in conjunction with FIG. 1 or 2. According to the example described in connection with FIG. 8, the maps of the stations I and II, as well as III and IV, are merged to generate a consolidated map.

Alternatively or additionally, the method 200 may include a step 230 for verifying the estimate of the estimated quantity of interest: such verification may be performed automatically or visually. Said verification step 230 may consist in detecting any significant discontinuity on a consolidated map. Alternatively or additionally, such verification step 230 may consist in automatically verifying that the values of estimates of said quantity of interest of the corresponding voxels are coherent, that is to say, that the values of such estimates are in a small range of values. Such verification can be performed using statistical tests, such as, by way of non-limiting examples, the Kolmogorov-Smirnov test or, preferably, the Bayesian theory. The method 200 may then include a step 231 to cause, via the output means, highlighting of the voxels, considered as little coherent in 230.

Thanks to the new estimates and/or maps presented above, the invention allows providing a practitioner with a set of relevant and consistent information, which could not be available using known techniques of the state of the art. This availability is made possible by adapting the processing unit 4 according to FIGS. 1 and 2 in that the processing means perform a method of estimating a quantity of interest involving the building of an arterial input function from perfusion data linked to one or more stations. Such implementation is advantageously made possible by uploading or storing within storage means cooperating with said processing means, a computer program product. The latter in fact comprises interpretable and/or executable instructions by said processing means. The interpretation or the execution of said instructions triggers the implementation of a method 100 or 200 in accordance with the invention. The means to communicate with the outside world of the processing unit can deliver a quantity of interest, namely, the estimated parameters 14, in a format adapted to the output means capable of outputting to a user 6, while said estimated quantity of interest may be advantageously output in the form of maps, for example, as illustrated in FIGS. 7 and 8.

Thanks to the invention, the data delivered are thus more numerous, consistent, reproducible and accurate. All the information available to a practitioner is thus likely to increase his confidence in determining a diagnosis and making decisions.

The invention claimed is:

1. A method for producing an estimate of a quantity of interest of an artery/tissue/vein dynamic system of an elementary volume—called a voxel—of an organ, said method being performed by a processor of a perfusion imaging analysis system, and comprising:
    obtaining perfusion data linked to a first station, the first station corresponding to a volume of the organ defined by an acquisition field of a magnetic resonance imaging device,
    moving the organ, relative to the magnetic resonance imaging device, to a location associated with a second station at which the acquisition field of a magnetic resonance imaging device defines a different respective volume of the organ,
    obtaining perfusion data linked to the second station,
    determining an arterial input function that is specific to at least one station among the plurality of said stations,
    building a joint arterial input function from said specific arterial input function, and
    estimating the quantity of interest by applying the joint arterial input function built from said specific arterial input function to data obtained from each of the plurality of stations.

2. The method according to claim 1, wherein the perfusion imaging analysis system comprises output means for a user of said system, said output means cooperating with the processor, said method comprising a subsequent step to cause an output to the joint arterial input function by said output means.

3. The method according to claim 1, comprising:
    a preliminary step for preprocessing the perfusion data, said step being arranged to correct said perfusion data.

4. A method for producing an estimate of a quantity of interest of an artery/tissue/vein dynamic system of a region of interest, said region comprising at least one voxel, said quantity of interest being estimated by voxel using the method according to claim 1.

5. The method according to claim 4, in which said region of interest extends over several stations among the plurality of stations.

6. The method according to claim 4, the perfusion imaging analysis system having output means for a user of said system, said output means cooperating with the processor, said method comprising a subsequent step to trigger an output of said estimated quantity of interest for the voxels of the region of interest by said output means.

7. A processing unit having communication means with the outside world and processing means cooperating with storage means, wherein:
the communication means are adapted to receive from the outside world perfusion data linked to a plurality of stations, each station being a volume corresponding to an acquisition field defined by a magnetic resonance imaging device; and
the storage means include instructions executable or interpretable by the processing means whose interpretation or execution of said instructions causes the implementation of a method according to claim 4.

8. A processing unit according to claim 7, in which the communication means deliver an estimated quantity of interest in a format suitable for output means adapted to output it to a user.

9. A perfusion imaging analysis system comprising a processing unit, according to claim 7, and output means configured to output to a user an estimated quantity.

10. A non-transitory computer readable medium encoded with a program comprising one or more instructions interpretable or executable by the processing means of a processing unit, said processing unit comprising storage means or cooperating with storage means, said program being loadable into said storage means, wherein the interpretation or execution of said instructions by said processing means triggers the implementation of a method according to claim 4.

11. The method according to claim 1, wherein said joint arterial input function is built from perfusion data linked to at least the first and second stations.

12. The method according to claim 1, wherein the joint arterial input function is built from arterial input functions that are respectively specific to each of at least two stations among said plurality of stations.

* * * * *